United States Patent
Schechner et al.

(10) Patent No.: US 9,758,435 B2
(45) Date of Patent: Sep. 12, 2017

(54) DENTAL CERAMIC ARTICLE, PROCESS OF PRODUCTION AND USE THEREOF

(75) Inventors: Gallus Schechner, Herrsching (DE); Holger Hauptmann, Sindelsdorf (DE); Rainer K. Dittmann, München (DE); Hans R. Schnagl, Jengen (DE)

(73) Assignee: 3M Innovative Properties Company, Saint Pau, MN (US)

( * ) Notice: Subject to any disclaimer, the term of this patent is extended or adjusted under 35 U.S.C. 154(b) by 70 days.

(21) Appl. No.: 14/003,409

(22) PCT Filed: Mar. 16, 2012

(86) PCT No.: PCT/US2012/029333
§ 371 (c)(1),
(2), (4) Date: Sep. 5, 2013

(87) PCT Pub. No.: WO2012/125885
PCT Pub. Date: Sep. 20, 2012

(65) Prior Publication Data
US 2013/0341812 A1    Dec. 26, 2013

(30) Foreign Application Priority Data

Mar. 17, 2011 (EP) .................................... 11158584

(51) Int. Cl.
*C04B 35/48* (2006.01)
*A61C 13/00* (2006.01)
(Continued)

(52) U.S. Cl.
CPC ................ *C04B 35/48* (2013.01); *A61C 5/77* (2017.02); *A61C 8/005* (2013.01);
(Continued)

(58) Field of Classification Search
None
See application file for complete search history.

(56) References Cited

U.S. PATENT DOCUMENTS

| 2,843,555 A | 7/1958 | Berridge |
| 3,159,662 A | 12/1964 | Ashby |

(Continued)

FOREIGN PATENT DOCUMENTS

| CA | 2380576 | 2/2001 |
| CN | 20091049708 | 4/2009 |

(Continued)

OTHER PUBLICATIONS

"Anti-adhering, anti-soiling coatings." *Eurobonding.* pp. 1-2. Web. Jul. 7, 2010. <http://www.eurobonding.org/Englisch/Oberflaechen/Ant_adheringi.htm>.

(Continued)

*Primary Examiner* — David Sample

(57) ABSTRACT

The present disclosure relates to a dental ceramic article comprising ceramic components, the ceramic components having ZrO2 and Al2O3 and at least one component comprising Mn, Er or mixtures thereof, Al2O3 being present in an amount below about 0.15 wt.-% with respect to the weight of the ceramic article. The present disclosure relates also to kit of parts comprising a ceramic article and a coloring solution and processes for producing a dental ceramic article.

11 Claims, 2 Drawing Sheets

(51) Int. Cl.

| | | |
|---|---|---|
| *A61C 8/00* | (2006.01) | |
| *A61C 5/10* | (2006.01) | |
| *A61K 6/00* | (2006.01) | |
| *A61K 6/02* | (2006.01) | |
| *C04B 35/486* | (2006.01) | |
| *C04B 35/632* | (2006.01) | |
| *C04B 35/634* | (2006.01) | |
| *C04B 41/00* | (2006.01) | |
| *C04B 41/50* | (2006.01) | |
| *C04B 41/85* | (2006.01) | |
| *A61C 5/77* | (2017.01) | |
| *C04B 111/00* | (2006.01) | |
| *C04B 111/82* | (2006.01) | |

(52) U.S. Cl.
CPC ........ *A61C 13/0022* (2013.01); *A61K 6/0094* (2013.01); *A61K 6/021* (2013.01); *A61K 6/024* (2013.01); *A61K 6/025* (2013.01); *C04B 35/486* (2013.01); *C04B 35/632* (2013.01); *C04B 35/63488* (2013.01); *C04B 41/009* (2013.01); *C04B 41/5007* (2013.01); *C04B 41/85* (2013.01); *C04B 2111/00836* (2013.01); *C04B 2111/82* (2013.01); *C04B 2235/3206* (2013.01); *C04B 2235/3208* (2013.01); *C04B 2235/3217* (2013.01); *C04B 2235/3224* (2013.01); *C04B 2235/3225* (2013.01); *C04B 2235/3227* (2013.01); *C04B 2235/3229* (2013.01); *C04B 2235/3262* (2013.01); *C04B 2235/3267* (2013.01); *C04B 2235/3272* (2013.01); *C04B 2235/449* (2013.01); *C04B 2235/61* (2013.01); *C04B 2235/612* (2013.01); *C04B 2235/77* (2013.01); *C04B 2235/9623* (2013.01); *C04B 2235/9661* (2013.01)

(56) References Cited

U.S. PATENT DOCUMENTS

| | | |
|---|---|---|
| 3,178,464 A | 4/1965 | Pierpoint |
| 3,220,972 A | 11/1965 | Lamoreaux |
| 3,250,808 A | 5/1966 | Moore, Jr. |
| 3,313,773 A | 4/1967 | Lamoreaux |
| 3,410,886 A | 11/1968 | Joy |
| 3,470,255 A | 9/1969 | Kelly |
| 3,492,394 A | 1/1970 | Heine |
| 3,567,755 A | 3/1971 | Seyfried |
| 3,646,085 A | 2/1972 | Bartlett |
| 3,671,007 A | 6/1972 | Bailey |
| 3,689,346 A | 9/1972 | Rowland |
| 3,715,334 A | 2/1973 | Karstedt |
| 3,775,452 A | 11/1973 | Karstedt |
| 3,810,874 A | 5/1974 | Mitsch |
| 3,814,730 A | 6/1974 | Karstedt |
| 3,814,731 A | 6/1974 | Nitzsche |
| 4,101,513 A | 7/1978 | Fox |
| 4,189,325 A | 2/1980 | Barrett |
| 4,276,252 A | 6/1981 | Kreis |
| 4,288,345 A | 9/1981 | Ashby |
| 4,313,988 A | 2/1982 | Koshar |
| 4,510,094 A | 4/1985 | Drahnak |
| 4,530,879 A | 7/1985 | Drahnak |
| 4,546,006 A | 10/1985 | Ohno |
| 4,550,030 A | 10/1985 | Ohi |
| 4,582,885 A | 4/1986 | Barber |
| 4,603,215 A | 7/1986 | Chandra |
| 4,640,939 A | 2/1987 | Cavezzan |
| 4,670,531 A | 6/1987 | Eckberg |
| 4,677,137 A | 6/1987 | Bany |
| 4,699,813 A | 10/1987 | Cavezzan |
| 4,705,765 A | 11/1987 | Lewis |
| 4,712,092 A | 12/1987 | Boldridge |
| 4,772,436 A | 9/1988 | Tyszblat |
| 4,828,117 A | 5/1989 | Panzera |
| 4,865,954 A | 9/1989 | Hagiwara |
| 4,916,169 A | 4/1990 | Boardman |
| 4,946,369 A | 8/1990 | Becl |
| 5,011,403 A | 4/1991 | Sadoun |
| 5,089,536 A | 2/1992 | Palazzotto |
| 5,091,033 A | 2/1992 | Nakabayashi |
| 5,091,483 A | 2/1992 | Mazurek |
| 5,106,303 A | 4/1992 | Odén |
| 5,183,597 A | 2/1993 | Lu |
| 5,219,805 A | 6/1993 | Yoshida |
| 5,250,352 A | 10/1993 | Tyszblat |
| 5,263,858 A | 11/1993 | Yoshida |
| 5,286,815 A | 2/1994 | Leir |
| 5,306,758 A | 4/1994 | Pellerite |
| 5,316,716 A | 5/1994 | Sato |
| 5,409,773 A | 4/1995 | Kessel |
| 5,447,967 A | 9/1995 | Tyszblat |
| 5,453,227 A | 9/1995 | Rieger |
| 5,565,152 A | 10/1996 | Odén |
| 5,618,585 A | 4/1997 | Hechler |
| 5,656,564 A | 8/1997 | Nakayama |
| 5,804,674 A | 9/1998 | Yamana et al. |
| 5,851,674 A | 12/1998 | Pellerite |
| 5,861,113 A | 1/1999 | Choquette |
| 5,869,548 A | 2/1999 | Ikushima |
| 5,932,150 A | 8/1999 | Lacey |
| 6,042,884 A | 3/2000 | Klein |
| 6,087,285 A | 7/2000 | Oomichi |
| 6,096,247 A | 8/2000 | Ulsh |
| 6,114,054 A | 9/2000 | Klein |
| 6,132,672 A | 10/2000 | Vignali |
| 6,204,350 B1 | 3/2001 | Liu |
| 6,277,485 B1 | 8/2001 | Invie |
| 6,358,874 B1 | 3/2002 | Kobayashi |
| 6,376,065 B1 | 4/2002 | Korba |
| 6,376,569 B1 | 4/2002 | Oxman |
| 6,403,382 B1 | 6/2002 | Zhu |
| 6,656,258 B2 | 12/2003 | Elsbernd |
| 6,673,287 B2 | 1/2004 | Breen |
| 6,709,694 B1 | 3/2004 | Suttor |
| 6,713,421 B1 | 3/2004 | Hauptmann |
| 6,737,170 B2 | 5/2004 | Fitch |
| 6,743,516 B2 | 6/2004 | Murphy |
| 6,769,912 B2 | 8/2004 | Beuschel |
| 6,783,719 B2 | 8/2004 | Robinson |
| 6,788,463 B2 | 9/2004 | Merrill |
| 6,860,956 B2 | 3/2005 | Bao |
| 6,974,549 B2 | 12/2005 | Ohgaki |
| 6,977,057 B2 | 12/2005 | Reitz |
| 7,014,799 B2 | 3/2006 | Yang |
| 7,057,832 B2 | 6/2006 | Wu |
| 7,173,778 B2 | 2/2007 | Jing |
| 7,294,731 B1 | 11/2007 | Flynn |
| 7,891,636 B2 | 2/2011 | Zhang |
| 2001/0044021 A1 | 11/2001 | Ogawa |
| 2002/0090515 A1 | 7/2002 | Pellerite |
| 2002/0190416 A1 | 12/2002 | Birch |
| 2003/0132539 A1 | 7/2003 | Althoff |
| 2003/0175551 A1 | 9/2003 | Smith |
| 2004/0119180 A1* | 6/2004 | Frank et al. .................... 264/16 |
| 2004/0157063 A1 | 8/2004 | Takahashi |
| 2004/0202865 A1 | 10/2004 | Homola |
| 2005/0048288 A1 | 3/2005 | Flynn |
| 2005/0089694 A1 | 4/2005 | Moffatt |
| 2005/0089696 A1 | 4/2005 | Bosshammer |
| 2006/0012079 A1 | 1/2006 | Jung |
| 2006/0046069 A1 | 3/2006 | Jung |
| 2006/0117989 A1 | 6/2006 | Hauptmann |
| 2006/0172901 A1 | 8/2006 | Kubota |
| 2007/0062410 A1 | 3/2007 | Thiel |
| 2007/0269747 A1 | 11/2007 | Bahdur |
| 2007/0292597 A1 | 12/2007 | Ritzberger |
| 2008/0145525 A1 | 6/2008 | Guo |
| 2008/0203271 A1 | 8/2008 | Okinaka |
| 2008/0203620 A1 | 8/2008 | Okinaka |
| 2008/0303181 A1 | 12/2008 | Holand |
| 2009/0068475 A1 | 3/2009 | Bosshammer |
| 2010/0055474 A1 | 3/2010 | Bachon |

(56) References Cited

U.S. PATENT DOCUMENTS

| | | | | |
|---|---|---|---|---|
| 2010/0209876 A1* | 8/2010 | Wagner et al. | ............ | 433/201.1 |
| 2010/0221683 A1 | 9/2010 | Franke et al. | | |
| 2011/0236860 A1* | 9/2011 | Jahns et al. | ................ | 433/222.1 |
| 2011/0319254 A1 | 12/2011 | Ritzberger | | |

FOREIGN PATENT DOCUMENTS

| | | |
|---|---|---|
| CN | 101870582 | 10/2010 |
| DE | 2012304 | 9/1971 |
| DE | 3109927 | 9/1982 |
| DE | 3424777 | 1/1985 |
| DE | 4320072 | 5/1994 |
| DE | 19619165 | 9/1997 |
| DE | 19619168 | 10/1997 |
| DE | 19938144 | 4/2001 |
| EP | 0047873 | 3/1982 |
| EP | 0238033 | 9/1987 |
| EP | 0455854 | 11/1991 |
| EP | 0630622 | 12/1994 |
| EP | 0816305 | 1/1998 |
| GB | 421872 | 1/1935 |
| JP | 02-014866 | 6/1988 |
| JP | 03-005366 | 1/1991 |
| JP | 03-170148 | 7/1991 |
| JP | 03-198841 | 8/1991 |
| JP | 04-280864 | 10/1992 |
| JP | 04-296336 | 10/1992 |
| JP | 06-140884 | 10/1992 |
| JP | 08-033650 | 2/1996 |
| JP | 10-001375 | 6/1996 |
| JP | 09-110563 | 4/1997 |
| JP | 09-142966 | 6/1997 |
| JP | 11-116328 | 4/1999 |
| JP | 2007106819 | 4/2007 |
| JP | 2008137306 | 6/2008 |
| WO | WO 99/37720 | 7/1999 |
| WO | WO 01/13862 | 3/2001 |
| WO | WO 01/30931 | 5/2001 |
| WO | WO 01/68940 | 9/2001 |
| WO | WO 2004/110959 | 12/2004 |
| WO | WO 2006/107082 | 10/2006 |
| WO | WO 2008/112400 | 9/2008 |

OTHER PUBLICATIONS

Aoshima. 1997. *PP&A.* 9(8):861-868. "Aesthetic All-Ceramic Restorations: The Internal Live Strain Technique".
Bhattacharya et al. Jun. 2005. *Journal of Microelectromechanical Systems.* 14(3):590-597. "Studies on Surface Wettability of Poly(Dimethyl) Siloxane (PMDS) and Glass Under Oxygen-Plasma Treatment and Correlation With Bond Strength".
Blum et al. *Principles of Electroplating and Electroforming (electrotyping).* 3rd Edition. McGraw-Hill Book Company. 1949. Print.
Bruggers. 1997. *Quintessence of Dental Technology.* 20:10-20. "Masters in Concert: Interview: Dr. Gerard Chiche and Mr. Hitoshi Aoshima".
Cales. 1998. *Bioceramics.* 11:592-594. "Colored Zirconia Ceramics for Dental Applications".
Chua et al. Feb. 2000. *Applied Physics Letters.* 76(6):721-723. American Institute of Physics. "Spontaneous Formation of Complex and Ordered Structures on Oxygen-Plasma-Treated Elastomeric Polydimethylsiloxane".
Clarson et al. *Siloxane Polymers.* Englewood Cliffs, NJ: PTR Prentice Hall, Inc., 1993. Print.
Craig. *Restorative Dental Materials.* 7th Edition. Chapter 17, pp. 432-449. St. Louis: The C.V. Mosby Company. 1985. Print.
Crivello et al. 1995. *Macromol. Symp.* 95:79-89. Huthig & Wepf Verlag, Zug. "Cationic Photopolymerization of Ambifunctional Monomers".
Ceramic Products Manufacturing. 1996.11.7.1-11.7.3. (Case No. 05 CV 1875 ADM/JJG).

Davies et al. 2003. *Proc. of SPIE.* 5183:94-108. "Application of Precision Diamond Machining to the Manufacture of Micro-Photonic Components".
Defendants' Identification of Claim Terms That Require Construction (Case No. 05 CV 1875 ADM/JJG).
Defendants' Proposed Claim Constructions (Case No. 05 CV 1875 ADM/JJG).
Defendant's Via Zahnfabrik H. Rauter GMBH & Co. KG and Vident, Inc.'s Prior Art Statement (Case No. 05 CV 1875 ADM/JJG).
Encyclopedia of Polymer Science and Technology. 1968. vol. 8. p. 651. John Wiley & Sons, Inc. "Electroplating".
Encyclopedia of Polymer Science and Engineering. 1989. vol. 15. pp. 234-243 and 252. John Wiley & Sons, Inc. "Silicones".
Expert Report of Russell A Giordano (Feb. 27, 2008) (26 pgs).
Extended European Search Report for EP 11158584.0 mailed Sep. 8, 2011.
Fulmer et al. *Tensile, Impact and Fatigue Performance of a New Water Atomized Low-Alloy Powder—Ancorsteel 85 HP.* pp. 1, 4. Riverton: Hoeganaes Corporation. 1990.
Hauptmann et al. 2011. *IADR/AADR/CADR 89th General Session, San Diego, Calif.* vol. 90 A "1684 Colour or Translucency: Zirconia Aesthetics Between the Poles?" Abstract.
Jacobine et al. *Topics in Applied Chemistry: Radiation Curing: Science and Technology.* Ed. Pappas, Ch. 5, pp. 200-214. New York: S.P. Plenum Press. 1992. Print. "Photopolymerizabel Silicone Monomers, Oligomers, and Resins".
Jiang et al. Jan. 3, 2010. *Nanoelectronics Conference (INEC), 2010 3rd International*, IEEE, Piscataway, NJ, USA. pp. 1413-1414. "The technology of improving the optical property for the zirconia dental ceramic".
Jiang et al. Jul. 26, 2011. *Journal of Wuhan University of Technology-Mater. Sci. Ed.; Materials Science Edition,* Wuhan University of Technology, Heidelberg. 26(4):690-695. "Influence of alumina addition on the optical property of zirconia/alumina composite dental ceramics".
Kley. 1997. *Microelectronic Engineering.* 34:261-298. Elsevier Science B.V. "Continuous Profile Writing by Electron and Optical Lithography".
Kosmac et al. Feb. 2000. *J. Biomed. Mater Res.* 53(4):304-313. "Strength and Reliability of Surface Treated Y-TZP Dental Ceramics".
Kumar. 1993. *Appl. Phys. Lett.* 14(4):2002-2004. American Institute of Physics. "Features of Gold Having Micrometer to Centimeter Dimensions Can Be Formed Through a Combination of Stamping With an Elastomeric Stamp and an Alkanethiol "Ink" Followed by Chemical Etching".
Lee et al. 2006. *Advanced Material.* 18:3115-3119. "Antiadhesion Surface Treatments of Molds for High Resolution Unconventional Lithography".
McLean. *The Science and Art of Dental Ceramics: Monographs III and IV.* pp. 7, 26. New Orleans: Louisiana State University School of Dentistry. 1978. Print.
McLean. *The Science and Art of Dental Ceramics*: pp. 7, 26. vol. I:; *The Nature of Dental Ceramics and their Clinical Use.* Chicago: Quintessence Publishing Co., Inc. 1979. Print.
McLean. *The Science and Art of Dental Ceramics*: pp. 7, 26. vol. II: *Bridge Design and Laboratory Procedures in Dental Ceramics.* Chicago: Quintessence Publishing Co., Inc. 1980. Print.
Mutobe. 1997. *Quintessence of Dental Technology.* 20:83-106. "In Harmony with Nature: Esthetic Restoration of a Nonvital Tooth with IPS-Empress All-Ceramic Material".
Nakumura et al. 1999. *Quintessence of Dental Technology.* pp. 83-93. "Clinical Applications of a Newly Developed Hybrid Ceramic Composite for Posterior Prostheses".
Naylor. *Introduction to Metal Ceramic Technology.* pp. 138-139. Carol Stream: Quintessence Publishing Co, Inc. 1992. Print.
Noll. *Chemistry and Technology of Silicones.* New York: Academic Press. 1968.
Ocãna et al. 1998. *Journal of the European Ceramic Society.* 18-821-830. "Preparation by Hydrolysis of Aerosols and Colour Properties of Cr-Doped and Co-Doped Zircon Powders".

(56) References Cited

OTHER PUBLICATIONS

Pamphlet relating to the Cerec System. "Okonomie durch Technologie".

Pamphlet relating to the Procera system.

Pappas. *Radiation Curing Science and Technology*. pp. 200-214. New York: Plenum Press. 1992. Print. "Photopolymerizable Silicone Monomers, Oligomers, and Resins".

Park et al. 2004. *INSM 2004, KAIST*, Daejeon, Korea. pp. 1-3. "Fabrication of PDMS Replica Using Nano Replication Printing Process and Vacuum Pressure-Difference Technique".

PCT International Search Report for PCT/US2008/073450 mailed Jan. 14, 2009.

PCT International Search Report for PCT/US2012/029333 mailed Jul. 26, 2012.

Plueddemann et al. 1959. *M. Am. Chem. Soc.* 81:2632-2635. "Epoxyorganosiloxanes".

Pocius et al. 1997. *Plastics Engineering*. 53(12):31-97. "Adhesion of Polymer Interfaces and Pressure Sensitive Adhesive Tapes".

Quake et al. 2000. *Science*. 290:1536-1540. "From Micro- to Nanofabrication With Soft Materials".

Rieger. 1993. *Industrie Diamanten Rundschau IDR Feb. 1993*. Aluminum and Zirkonoxidkeramik in der Medizin. "Aluminum and Zirconium Oxide Ceramics in Medicine".

Schaefer et al. 1942. *Journal of Applied Physics*. 13:427-433. "Surface Replicas for Use in the Electron Microscope".

Sorenson et al. 1998. *Journal of the California Dental Association*. 26(3):207-214. "In-Ceram Fixed Partial Dentures: Three-Year Clinical Trial Results".

"The Vitadur® Technique, Working Instructions," $5^{th}$ ed. (pub'd Sep. 1990).

Tomanek. *Silicone & Industry, A Compendium for Practical Use, Instruction and Reference*. Munich: Walter Chemi GmbH. 1993. Print.

"Uses of antisoiling coating." *DuPont*™. pp. 1-2. 2007.

Vasilets et al. 1997. *Polymer*. 39(13):2875-2881. "Improvement of the Micro-Wear Resistance of Silicone by Vacuum Ultraviolet Irradiation".

"VITA-Hi-Ceram Working Instructions" (pub'd Aug. 1990).

Wilkinson. *Comprehensive Organometallic Chemistry*. vol. 2, pp. 329-330. New York: Pergamon Press, Ltd. 1982. Print. "Silicones".

Xi et al. Mar. 1, 2007. *ARC*. pp. 1-2. "Optical thin-film material with low refractive index for broadband elimination of Fresnel reflection".

Xia et al. 1998. *Angew. Chem. Int. Ed.* 37: 550-575. Wiley-VCH Verlag GmbH, D-69451 Weinheim. "Soft Lithography".

Yamamoto. *Metal-Ceramics*. Chicago: Quintessence Publishing Co., Inc. 1985. Print.

Yan et al. 2005. *Langmuir*. 21(19):8905-8912. American Chemical Society. "$CF_4$ Plasma Treatment of Poly(dimethylsiloxane): Effect of Fillers and Its Application to High-Aspect-Ratio UV Embossing".

Zhao et al. 1997. *J. Mater. Chem.* 7(7):1069-1074. "Soft Lithographic Methods for Nano-Fabrication".

\* cited by examiner

DENTAL CERAMIC ARTICLE, PROCESS OF PRODUCTION AND USE THEREOF

CROSS REFERENCE TO RELATED APPLICATIONS

This application is a national stage filing under 35 U.S.C. 371 of International Application No. PCT/US2012/029333, filed Mar. 16, 2012, which claims priority to European Application No. 11158584.0 filed Mar. 17, 2011. The disclosures of both applications are incorporated by reference in their entirety herein.

FIELD OF THE INVENTION

The invention relates to a coloured ceramic material having a beneficial combination of high strength and brightness making it in particular useful for dental applications. More specifically the invention relates to a ceramic zirconia material containing a low amount of alumina and coloured oxides selected from erbium, praseodymium, manganese and mixtures thereof.

BACKGROUND

Dental restorations containing oxide ceramics are known since a couple of years. Especially zirconia has been used for manufacturing dental ceramic support structures.

For the production or colouring of aesthetic dental restorations based on oxide ceramics different processes have been suggested.

WO 2004/110959 (corresponding to US 2006/117989 A1) relates to a colouring solution for ceramic framework. The solution comprises a solvent, a metal salt and polyethylene glycol having a molecular weight in the range of 1.000 to 200.000.

WO 00/46168 A1 (corresponding to refers to colouring ceramics by way of ionic or complex-containing solutions containing defined concentrations of at least one salts or complexes of the rare earth elements or of the elements of the subgroups. The solution might contain additives like stabilizers, complex builders, pigments and beating additives.

Similar approaches are described in US 2010/0221683 A1 (Franke), US 2007/0062410 A1 (Thiel) and U.S. Pat. No. 6,709,694.

US 2010/221683 describes a colouring solution for colouring a dental ceramic article, wherein the solution comprises a solvent and a colouring agent comprising rare earth element metals or ions and transition metals or ions. The dental ceramic article may comprise $ZrO_2$ and/or $Al_2O_3$.

U.S. Pat. No. 6,713,421 relates to blanks comprising zirconium oxide-based ceramic with an addition of 0.1 to 0.50 wt % of at least one of the oxides of the elements aluminium, gallium, germanium, indium and their use.

US 2007/0292597 A1 (Ritzberger) describes a process for the preparation of blanks and dental shaped parts which contain colouring compounds, wherein the process comprises the steps of a) coating an oxide powder with a colouring substance to produce a coloured powder, b) pressing the coloured powder to produce a shaped body and c) sintering the compressed body.

CN 101870582 (The 9th People's Hospitoal) describes a preparation method for tooth coloured dental ceramics based on Y-TZP powder using the rare earth metal oxides Pr6l1, $CeO_2$, $Er_2O_3$ and $MnO_2$.

U.S. Pat. No. 5,219,805 relates to an ivory-colored zirconia sintered body which contains as a main component stabilizer-containing $ZrO_2$ and based on the stabilizer-containing $ZrO_2$ certain amounts of $Er_2O_3$, $Pr_6O_{11}$, $Fe_2O_3$ and ZnO.

WO 01/12097 (corresponding to AU 200072766) relates to a process for the preparation of dentures comprising the steps of a) preparation of a blank, b) processing the blank by milling methods, c) dense sintering the blank in a certain temperature range, wherein the blank comprises a pre-sintered material having a certain raw-breaking resistance. The pre-sintered blank may comprise a zirconium oxide or aluminium oxide ceramic.

However, there is still room for improvement especially with regard to the requirements to be fulfilled with respect to modern dental materials. Many of the commercially available dental restorations still do not show the appearance of natural dental teeth.

Thus, it is generally an object of the invention to provide a dental article which can be used for making aesthetic dental restorations.

SUMMARY OF INVENTION

According to one embodiment it would be desirable to provide a ceramic article having improved brightness.

In this respect the invention relates to a dental ceramic article comprising ceramic components, the ceramic components comprising $ZrO_2$ and $Al_2O_3$ and at least one component comprising Mn, Er, or mixtures thereof. $Al_2O_3$ is present in an amount of about 0.001 wt.-% to about 0.15 wt.-% with respect to the weight of the ceramic components.

Another aspect of the invention features a kit of parts comprising at least one dental ceramic article and at least one colouring solution, the ceramic article comprising ceramic components, the ceramic components comprising $ZrO_2$ and $Al_2O_3$, $Al_2O_3$ in an amount up to about 0.15 wt.-% with respect to the weight of the ceramic article, the colouring solution comprising colouring components, the colouring components comprising ions selected from Mn, Er, and mixtures thereof.

A further aspect of the invention deals with a process for producing a dental ceramic article, the process comprising the step of treating a ceramic article with a colouring solution, the ceramic article comprising $ZrO_2$ and $Al_2O_3$, $Al_2O_3$ in an amount up to about 0.15 wt.-% with respect to the weight of the ceramic article, the colouring solution comprising at least one colouring component comprising ions selected from Er, Mn and mixtures thereof.

The invention also relates to a process for producing a dental ceramic article, the process comprising the steps of mixing at least one colouring component with ceramic components thereby obtaining a mixture, the at least one colouring component comprising ions or oxides selected from Er, Mn and mixtures thereof, the ceramic components comprising $ZrO_2$ and $Al_2O_3$, $Al_2O_3$ in an amount of up to about 0.15 wt.-% with respect to the weight of the ceramic components and shaping the mixture to form a ceramic article.

The invention is also related to the use of ceramic components or of a colouring solution in a colouring process, the colouring process comprising the step of treating the ceramic components with a colouring solution, the ceramic components and the colouring solution being as described in the present text.

The invention is also related to the use of a colouring solution or of ceramic components for improving the aesthetic appearance (e.g. brightness and/or remission properties) of a dental ceramic article, the colouring solution and the ceramic components being as described in the present text.

DESCRIPTION OF INVENTION

Figure 1:
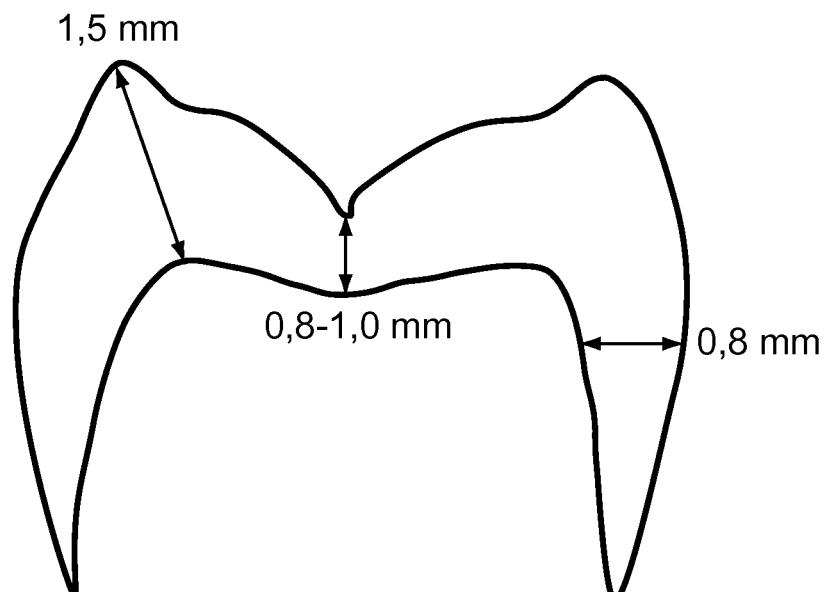
FIG. 1 shows the construction of a coloured crown sample

Unless otherwise specified, within the context of the text of the invention, the following terms have the following meanings.

The term "dental ceramic article" means any article which can or is to be used in the dental field, especially for producing or as dental restoration, a tooth model and parts thereof. Examples of dental articles include crowns, bridges, inlays, onlays, facings, abutments, implants and dental mill blanks. The surface of a tooth is considered not to be a dental article.

By "dental mill blank" is meant a solid block (3-dim article) of material from which a dental article, dental workpiece, dental support structure or dental restoration can be machined. A dental mill blank may have a size of about 20 mm to about 30 mm in two dimensions, for example may have a diameter in that range, and may be of a certain length in a third dimension. A blank for making a single crown may have a length of about 15 mm to about 30 mm, and a blank for making bridges may have a length of about 40 mm to about 80 mm. A typical size of a blank as it is used for making a single crown has a diameter of about 24 mm and a length of about 19 mm. Further, a typical size of a blank as it is used for making bridges has a diameter of about 24 mm and a length of about 58 mm. Besides the above mentioned dimensions, a dental mill blank may also have the shape of a cube, a cylinder or a cuboid. Larger mill blanks may be advantageous if more than one crown or bridge should be manufactured out of one blank. For these cases, the diameter or length of a cylindric or cuboid shaped mill blank may be in a range of about 100 to about 200 mm, with a thickness being in the range of about 10 to about 30 mm.

"Ceramic" means an inorganic non-metallic material that is produced by application of heat. Ceramics are usually hard, porous and brittle and, in contrast to glasses or glass ceramics, display an essentially purely crystalline structure.

"Glass" means an inorganic non-metallic amorphous material which is thermodynamically an under-cooled and frozen melt. Glass refers to a hard, brittle, transparent solid. Typical examples include soda-lime glass and borosilicate glass. A glass is an inorganic product of fusion which has been cooled to a rigid condition without crystallizing. Most glasses contain silica as their main component and a certain amount of glass former "Glass-ceramic" means an inorganic non-metallic material where one or more crystalline phases are surrounded by a glassy phase so that the material comprises a glass material and a ceramic material in a combination or mixture. Thus, a glass ceramic is a material sharing many properties with both glass and more traditional crystalline ceramics. It is formed as a glass, and then made to crystallize partly by heat treatment. Glass ceramics may refer to a mixture of lithium-, silicon-, and aluminium-oxides.

By "machining" is meant milling, grinding, cutting, carving, or shaping a material by a machine. Milling is usually faster and more cost effective than grinding. A "machinable article" is an article having a 3-dimensional shape and having sufficient strength to be machined.

A "powder" means a dry, bulk solid composed of a large number of fine particles that may flow freely when shaken or tilted.

A "particle" means a substance being a solid having a shape which can be geometrically determined. The shape can be regular or irregular. Particles can typically be analysed with respect to e.g. grain size and grain size distribution.

"Density" means the ratio of mass to volume of an object. The unit of density is typically $g/cm^3$. The density of an object can be calculated e.g. by determining its volume (e.g. by calculation or applying the Archimedes principle or method) and measuring its mass.

The volume of a sample can be determined based on the overall outer dimensions of the sample. The density of the sample can be calculated from the measured sample volume and the sample mass. The total volume of glass ceramic material can be calculated from the mass of the sample and the density of the used material. The total volume of cells in the sample is assumed to be the remainder of the sample volume (100% minus the total volume of material).

A dental ceramic article is classified as "pre-sintered" if the dental ceramic article has been treated with heat (temperature range from about 900 to about 1100° C.) for about 1 to about 3 h to such an extend that the raw breaking resistance (Weibull strength Sigma 0) of the dental ceramic article is within a range of about 15 to about 55 MPa or about 30 to about 50 MPa (measured according to the "punch on three ball test" (biaxial flexural strength) described in DIN EN ISO 6872, edition March 1999, with the following modifications: diameter of steel ball: 6 mm; diameter of support circle: 14 mm; diameter of flat punch: 3.6 mm; diameter of sample disc: 25 mm, thickness of sample disc: 2 mm; no grinding and polishing of samples.).

A pre-sintered dental ceramic article typically has a porous structure and its density (usually 3.0 $g/cm^3$ for an Yttrium stabilized $ZrO_2$ ceramic) is less compared to a completely sintered dental ceramic framework (usually 6.1 $g/cm^3$ for an Yttrium stabilized $ZrO_2$ ceramic). The diameter of the pores can be in a range of about 50 nm to about 150 nm (corresponding to about 500 to about 1500 Å). A typical pore diameter is about 120 nm.

A dental ceramic framework is classified as "absorbent" if the dental ceramic framework is able to absorb a certain amount of a liquid, comparable to a sponge. The amount of liquid which can be absorbed depends e.g. on the chemical nature of the dental ceramic framework, the viscosity of the solvent, the porosity and pore volume of the dental ceramic framework. E.g. a pre-sintered dental ceramic article, that is an article which has not been sintered to full density, is able to absorb a certain amount of liquid. Absorbing of liquids is typically only possible if the article has an open-porous structure.

A "porous material" refers to a material comprising a partial volume that is formed by voids, pores, or cells in the technical field of ceramics. Accordingly an "open-celled" structure of a material sometimes is referred to as "open-porous" structure, and a "closed-celled" material structure sometimes is referred to as a "closed-porous" structure. It may also be found that instead of the term "cell" sometimes "pore" is used in this technical field. The material structure categories "open-celled" and "closed-celled" can be determined for different porosities measured at different material samples (e.g. using a mercury "Poremaster 60-GT" from Quantachrome Inc., USA) according to DIN 66133. A material having an open-celled or open-porous structure can be passed through by e.g. gases.

Typical values for an "open-celled" material are between about 6% and about 35%, of between about 15% and about 35%, or between about 30% and about 35%.

The term "closed-celled" relates to a "closed porosity". Closed cells are those cells which are not accessible from the outside and cannot be infiltrated by gases under ambient conditions.

The unit "cells per mm$^2$" is related to the number of cells present on a cross section of the sample to be analysed. A suitable test method is given in DIN 13925.

The terms "sintering" or "firing" are used interchangeably. A pre-sintered ceramic framework shrinks during a sintering step, that is, if an adequate temperature is applied. The sintering temperature to be applied depends on the ceramic material chosen. For $ZrO_2$ based ceramics a typical sintering temperature range is about 1100° C. to about 1550° C. $Al_2O_3$ based ceramics are typically sintered in a temperature range of about 1300° C. to about 1700° C. Glass ceramic materials are typically sintered in a range of about 700 to about 1100° C. for about 1 to about 3 hours. Sintering typically includes the densification of a porous material to a less porous material (or a material having less cells) having a higher density, in some cases sintering may also include changes of the material phase composition (for example, a partial conversion of an amorphous phase toward a crystalline phase).

A "colouring agent" means any agent, which is able to lead to a colour change of a dental ceramic framework either right after treatment of the ceramic framework with the colouring agent or after a firing step of the treated dental ceramic framework.

Transition metals of the groups IIIA, IVA, VA, VIA, VIIA, VIIIA, IB, IIB (according to the former IUPAC classification) comprise the metals listed in the columns of the Periodic Table of Elements starting with the elements Sc, Ti, V, Cr, Mn, Fe, Co, Ni, Cu and Zn and the metals listed below those elements. According to the new IUPAC classification these columns are numbered as 3, 4, 5, 6, 7, 8, 9, 10, 11 and 12. According to the invention, the term "transition metals or ions" do not comprise "rare earth element metals or ions".

The terms "metal" or "metal ions" or "metal cations" are used interchangeably depending on the context and the present conditions. Depending on the solution and the presence or absence of other components (such as complexing agents), the metal can be present as such (i.e. in pure element form) or as ion or cation usually having a charge of +1, +2, +3 or +4.

A dental ceramic framework can be characterized as "homogeneously coloured" within the meaning of the invention, if no colour spots can be identified with the human eye on the surface of the dental ceramic framework after the sintering process.

A dental ceramic framework has a "tooth like colour" within the meaning of the invention if its colour can be classified by the VITA™ shading system under daylight conditions known to the dental technician.

A composition or solution is "essentially free of" a certain component within the meaning of the invention, if the composition or solution does not contain said component as an essential feature. Thus, said component is not willfully added to the composition or solution either as such or in combination with other components or ingredient of other components. A composition being essentially free of a certain component usually contains the component in an amount of less than about 0.1 wt.-% or less than about 0.01 wt.-% or less than about 0.001 wt.-% with respect to the whole composition. Ideally the composition or solution does not contain the said component at all. However, sometimes the presence of a small amount of the said component is not avoidable e.g. due to impurities.

"Ambient conditions" mean the conditions which the inventive solution is usually subjected to during storage and handling. Ambient conditions may, for example, be a pressure of about 900 to about 1100 mbar, a temperature of about −10 to about 60° C. and a relative humidity of about 10 to about 100%. In the laboratory ambient conditions are adjusted to about 20 to about 25° C. and about 1000 to about 1025 mbar.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

The invention provides a couple of advantages.

It was found that the ceramic article (dental restoration) described in the text of the invention typically shows an enhanced aesthetic appearance compared to ceramic articles (dental restorations) of the prior art. Particularly with non uniform shapes like dental crowns with varying material thicknesses the inventive coloured material exhibits an improved colour impression and light transmission especially in those areas having a greater wall thickness of the article (e.g. the cusps of a dental crown).

If desired, this surprising observation can be substantiated by measuring the optical remission spectra of coloured sample platelets. At a given thickness of the platelets (example here thickness 1.5 mm, diameter 12 mm), the new materials—when compared to prior materials that are adjusted to a similar overall colour appearance—show less remission over the visible range of wavelengths. This means more light can penetrate through the material and is absorbed by the colour of the material itself or the black background of the spectrophotometer device.

The beneficial properties of the invention might also be proven by determining the remission of light with respect to varying sample thicknesses.

Without wishing to be bound to a certain theory, it is believed that the combination of a comparably low alumina content with certain rare earth metals or rare earth metal oxides contributes to this effect.

The invention also provides the possibility of colouring dental ceramics with colouring solutions being essentially free of iron. Nevertheless, it was found that ceramic dentures with beneficial aesthetics can be obtained.

This finding is in contrast to the references and documents outlined above.

E.g. CN 101870582 only describes 3Y-TZP ceramic materials. Those materials contain Al2O3 in an amount of about 0.25 wt.-%.

The same is true for US 2007/0292597 (Ritzberger) and U.S. Pat. No. 6,709,694 (Suttor) which uses partially stabilized ZrO2 powders e.g. TZ3-YSB-C from the company Tosoh containing Al2O3 in an amount of 0.2 to 0.5 wt.-%.

The LAVA™ Frame Zirconia material used in US 2010/0221683 (Franke) is also based on a 3Y-TZP ceramic material. Thus, none of those documents describe the specific combination of a ZrO2 based ceramic material containing only a small amount of Al2O3 in combination with specific colouring additives. The invention relates to a ceramic article, especially a dental ceramic article or a ceramic article for use in the dental field. The ceramic article comprises ceramic components. Oxides which are present in the ceramic article are ZrO2 (including traces of HfO2), Al2O3, and suitable stabilizers including Y2O3.

According to one embodiment, the ceramic article only contains traces of Al2O3.

Al2O3 is typically present in an amount below about 0.15 wt.-% or below about 0.14 wt.-% or below about 0.13 wt.-% or below about 0.12 wt.-% or below about 0.11 wt.-% or below about 0.1 wt.-%, wt.-% with respect to the weight of the ceramic components.

Typical ranges for Al2O3 include from 0.0001 to about 0.15 wt.-% or from about 0.001 to about 0.14 wt.-% or from about 0.01 to about 0.13 wt.-% or from about 0.1 to about 0.10 wt.-%.

If the content of alumina is outside the above range, in particular present in an amount above about 0.15 wt.-%, it can be difficult to achieve the desired aesthetic properties.

The ceramic article also comprises at least one component selected from Mn, Er, Pr and mixtures thereof. It can be advantageous, if not only one of these components is present but a mixture thereof, e.g. a) Mn and Er, b) Mn and Pr, c) Er and Pr or e) Mn, Er and Pr. Option e)—that is, if Mn, Er and Pr are present together—can be preferred.

Depending on the manufacturing process applied, these components are typically present as oxides or as ions.

The ceramic article can be in a sintered or pre-sintered stage. If the ceramic article is in a sintered stage Mn, Er and Pr are typically present as oxides.

The ceramic article may also comprise a stabilizer.

Components which can be used as stabilizers comprise Y, Mg, Ca, Ce, La, combinations (e.g. mixed oxides or alloys) and mixtures thereof.

Using e.g. yttrium stabilized zirconia can be advantageous due to its ability to stabilize certain crystal structures of the zirconia material and thus enabling the practitioner to provide materials with high strengths.

The stabilizer can be present in the dental article in an amount of about 1 to about 8 mol % or of about 1.5 to about 6 mol % or of about 2 to about 5 mol %.

According to one embodiment, the ceramic article may further be characterized by at least one of the following features (in the sintered ceramic, all components are present as oxides):

ZrO2+HfO2: from about 80 wt.-% to about 98 wt.-% or from about 85 wt.-% to about 97 wt.-%, (with HfO2 being typically in a range from about 0.0001 to about 3 wt.-% with respect to the weight of the ceramic article)

Al2O3: from 0.0001 to about 0.15 or from about 0.0001 to about 0.14 wt.-% or from about 0.001 to about 0.12 wt.-%, Er2O3: from about 0.010 wt.-% to about 1.5 wt.-% or from about 0.020 wt.-% to about 1.2 wt.-%, Pr6O11: from about 0 wt.-% to about 0.1 wt.-% or from about 0.0001 wt.-% to about 0.06 wt.-%, MnO2: from about 0 wt.-% to about 0.01 wt.-% or from about 0.0001 wt.-% to about 0.005 wt.-%, Fe2O3: from about 0 wt.-% to about 0.1 wt.-% or from about 0.0001 wt.-% to about 0.1 wt.-% or from about 0.001 to about 0.8 wt.-%, Stabilizer: from about 1 wt.-% to about 10 wt.-% or from about 2 wt.-% to about 7 wt.-% (especially if the stabilizer comprises Y2O3).

According to one embodiment the ceramic article is in a pre-sintered stage or in a stage which allows the ceramic article to be machined. Thus, the ceramic article should have a sufficient raw breaking resistance. This stage is sometimes also called "green body". That is, the material may have already been slightly fired to a certain temperature to increase the raw breaking resistance of the material.

If desired, pre-sintering can be carried out in a temperature range from about 700° C. to about 1100° C. or from about 800° C. to about 1000° C.

The ceramic article can be produced by any standard procedure known to the person skilled in the art, including uniaxial pressing, cold isostatic pressing (CIP), rapid-prototyping and slip casting.

If the ceramic article is in a pre-sintered stage (i.e. before having conducted a final sintering or firing step), it can typically be characterized by at least one or more of the following features:

raw breaking resistance: from about 5 to about 55 MPa, or from about 5 to about 30 MPa, density: from about 2.4 to about 3.7 g/cm$^3$, or from about 2.5 to about 3.6 g/cm$^3$, porosity: from about 40 to about 60 vol.-%.

The pore diameter is typically in a range from about 10 nm to about 500 nm or from about 50 to about 200 nm. According to one embodiment, the average pore diameter is usually in a range of about 100 nm.

If the ceramic article has been sintered to its final stage, it typically fulfils at least one of the following physical parameters:

breaking resistance: at least about 400 MPa, or at least about 700 MPa or at least about 1000 MPa, density: from about 5.9 to about 6.1 g/cm$^3$ or from about 6.0 to about 6.1 g/cm$^3$, and/or light emission, in particular, fluorescence emission with bands in the region of the visible light (e.g. from about 400 nm to about 800 nm).

If desired, these parameters can be measured as follows:

The breaking resistance of the sintered dental ceramic article can be determined according to the "punch on three ball test" (biaxial flexural strength) described in DIN EN ISO 6872, edition March 1999, with the following modifications: diameter of steel ball: 3 mm; diameter of support circle: 12 mm; diameter of flat punch: 3.6 mm; diameter of sample disc: 16 mm, thickness of sample disc: 1.6 mm (+/−0.05 mm); grinding of samples with 10 µm disc to be +/−0.05 mm plan parallel and polishing of samples consecutively with 9 and 3 µm.

The density can be obtained from determining the mass (by weighing) and the volume (e.g. by calculation or using the "Archimedes Method").

The fluorescence properties can be determined using an optical setup comprising the following parts (particularly suited for sharp emission bands): GC America G-Light as light source, irradiating light of around 409 nm wavelength, an Ulbricht sphere, fiber optics from Topsensor Systems as light conductor and an A/D converter. A sample having the shape of a disc (diameter of 16 mm, thickness of 1.6 mm) can be used to cover the opening of the Ulbricht sphere. The light emission spectrum of the sample can be measured while trans-illuminating it with exitation radiation (violet light). Excitation radiation of shorter wavelengths is also suited for fluorescence measurements.

For spectra with broader emission bands the samples can alternatively be placed in an UV-light box used for inspection of thin layer chromatography plates. If desired, fluorescence can also be detected by the human eye as by the lightening up of the sample against the black background.

Another option is to measure the remission spectrum e.g. with a spectrophotometer (e.g. Colour i7). Typically two measurements are done: one remission spectrum using irradiation e.g. of the D65 light source including the UV range and one remission spectrum with irradiation e.g. of the D65 light source excluding the UV range. Subsequently both spectra are subtracted from each other, the yielding curve showing the fluorescent effect(s).

If desired, the aesthetic properties of the dental ceramic material can also be evaluated by a panel of practitioners in a standardized environment using statistical methods.

The ceramic article may have different shapes. Shapes of dental articles include dental support structure(s), dental crown(s), dental bridge(s), mill blank(s), implant(s), abutment(s), onlay(s) or inlay(s).

If the ceramic article has the shape of a mill blank, the mill blank is typically contained in a holding device like a frame or fixed on a stub.

Holding devices including frames have been proven to be useful. Sometimes it can be desirable, if the mill blank is put in a magazine, either for storing or for machining. The holding device may facilitates the machining of the ceramic article, e.g. by a machining device such as a milling device. Examples of holding devices are shown in US 2003/0132539, U.S. Pat. No. 6,769,912 and EP 0 455 854 B1. The content of these documents with regard to holding devices (e.g. frames and stubs or supporting body) is herewith incorporated by reference and regarded part of the text of the present invention.

Fixing of the ceramic article on a stub can be achieved e.g. by gluing. The fixing should be such that the ceramic article can be processed in a milling machine e.g. on a Cerec™ InLab machine available from Sirona AG, Bensheim, Germany.

Suitable ways for the manufacturing or production of the ceramic article include the following processes:

The ceramic article may be produced by a process comprising the step of treating a ceramic article with a colouring solution The ceramic article is as described in the present text and comprises ZrO2 and Al2O3, Al2O3 in an amount below about 0.1 wt.-% with respect to the weight of the ceramic components.

The colouring solution comprises colouring components comprising ions selected from Mn, Er and mixtures thereof.

The colouring ions selected from Mn, Er and mixtures thereof are typically present in an amount of at least about 0.001 or at least about 0.005 or at least about 0.01 mol/L.

The respective ions may be present in an amount of up to about 0.6 or up to about 0.5 or up to about 0.4 mol/L Thus, useful ranges for those ions include from about 0.001 to about 0.6 or from about 0.05 to about 0.5 or from about 0.1 to about 0.4 mol/L.

The colouring ions selected from Mn, Er, and mixtures thereof are typically present in an amount of at least about 0.10 or at least about 0.15 or at least about 0.2 wt.-% with respect to the weight of the colouring solution.

The respective ions may be present in an amount of up to about 10 or up to about 8 or up to about 7 wt.-% with respect to the weight of the colouring solution.

Useful ranges for those ions include from about 0.10 to about 10 or from about 0.15 to about 8 or from about 0.2 to about 7 wt.-%.

If the content of those ions in the colouring solution is outside these ranges, the desired brightness of the ceramic article treated with the colouring solution might be difficult to be obtained.

In particular, an amount above about 10 wt.-% may result in too strong colours.

On the other hand, an amount below about 0.1 wt.-% may result in colours that are too light even for bleach shades.

Besides Mn and/or Er ions, the colouring solution may comprise further rare earth element metals or ions selected from La, Ce, Nd, Sm, Eu, Gd, Tb, Dy, Ho, Tm, Yb, Lu and mixtures thereof.

The amount of metal ions contained in the colouring solution should be sufficient to achieve an adequate colouring of the ceramic framework, especially after a firing process. The overall amount of colouring agent used is not particularly limited unless the result to be achieved cannot be obtained.

Good results can be achieved e.g. with an overall amount or colouring agent being present in the colouring solution in a range of about 0.01 to about 20 wt.-% of metal ions, or in the range of about 0.1 to about 17.0 wt.-%, or in the range of about 1 to about 15 wt.-% or in the range of about 2 to about 13 wt.-% with respect to the weight of the whole composition.

The metals or ions are present in the colouring solution in an amount of at least about 0.05 mol/l solvent or at least about 0.06 mol/l solvent at least about 0.07 mol/l or at least about 0.08 mol/l or at least about 0.1 mol/l or at least about 0.2 mol/l solvent.

There is no specific upper limit for the metals or ions being present in the colouring solution. Preferably, the amount should be such that a storage stable solution can be obtained. Typically, the upper amount does not exceed a value of about 1 mol/l solvent or about 0.8 mol/l solvent or about 0.7 mol/l solvent or about 0.6 mol/l solvent.

The metals or ions are present in the solution in an amount of about 0.00001 to about 0.05 mol/l solvent or in an amount of about 0.0001 to about 0.03 mol/l solvent or in an amount of about 0.0005 to about 0.02 mol/l solvent or in an amount of about 0.0008 to about 0.01 mol/l solvent.

Usually, the colouring agent comprises salts comprising cations and anions. Anions which were found to be useful include $Cl^-$, $OAc^-$, $NO_3^-$, $NO_2^-$, $CO_3^{2-}$, $HCO_3^-$, $ONC^-$, $SCN^-$, $SO_4^{2-}$, $SO_3^{2-}$, gluturate, lactate, gluconate, propionate, butyrate, glucuronate, benzoate, phenolate.

Using anions which do not produce corrosive gases during a heating or sintering process can be beneficial.

The colouring solution may also comprise a solvent.

The solvent should be able to at least partially dissolve the components of the composition, especially the colouring agent(s) selected.

Typical solvents which can be used either alone or in admixture include water, alcohols like methyl alcohol, ethyl alcohol, iso-propyl alcohol, n-propyl alcohol, polar aprotic liquids like ketones such as acetone, ethylacetate and mixtures of water with alcohols and/or ketones. Preferred solvents which can be used in pure form include e.g. water and alcohols. Examples of useful mixtures of solvents include water and ethyl alcohol.

The amount of solvent used is not particularly limited unless the result to be achieved cannot be obtained.

A typical colouring solution according to the invention contains at least about 60 wt.-% solvent or least about 75 wt.-% solvent or least about 90 wt.-% solvent with respect to the weight of the whole composition.

The inventive colouring solution can also comprise adjuvants like stabilizers (including methoxy phenol hydrochinone or Topanol A), temporary binders, buffers (including acetate or amino buffers) or thixotropic substances (including polysaccharides, poly vinyl alcohols, polyethylenglycols (PEG), cellulose derivatives).

There is no need that any of these additives is present, however, they can be present. If they are present (that is, the amount of additive is greater than about 0.01 wt.-%), they are usually present in an amount up to about 4 wt.-% or up to about 6 wt.-% or up to about 12 wt.-% with respect to the weight of the whole composition.

The pH-value of the colouring solution comprising water as a solvent is not particularly limited. Examples of useful pH-values are equal or greater than 1 or 2 or 3 or 4 or 5 or 6 or 7 or 8 or 9. Thus, the pH-value can be in a range of about 1 to about 9 or in the range of about 2 to about 8. Measurement of the pH-value can be achieved by means known by the person skilled in art. E.g. an instrument like Metrohm™ 826 or pH mobile indicator paper can be used.

The colouring solution should also have an adequate viscosity so that sufficient wetting of and penetration into the pores of the dental ceramic framework can be achieved. Good results can be obtained with a solution having a dynamic viscosity of about 1.0 mPa*s up to about 100 mPa*s or up to about 80 mPa*s or up to about 60 mPa*s.

The dynamic viscosity can be determined with a Physica MCR301 instrument using a cone plate geometry, diameter 50 mm, angle (cone) 1°, at 23° C. A typical shear rate is 200 rounds/s, however, generally the viscosity of liquids is independent from the shear rate in a wide range.

If the viscosity of the colouring solution is too high, the colour value of the coloured dental ceramic framework might be too bright. If the viscosity of the colouring solution is too low, the colour value of the coloured dental ceramic framework might be not homogenous.

According to one embodiment, the colouring solution can comprise
- a solvent in an amount of about 60 to about 96 or in an amount of about 70 to about 94 or in an amount of about 80 to about 90 wt.-%,
- a colouring agent comprising at least one of Mn (ions), Er (ions) and mixtures thereof, in an amount of about 0.1 to about 20 or in an amount of about 0.5 to about 10 or in an amount of about 0.9 to about 5.0 wt.-%,
- optionally additives (like e.g. stabilizers, temporary binders, buffers and/or thixotropic substances) in an amount of about 0.1 to about 12 or in an amount of about 1 to about 6 or in an amount of about 2 to about 4 wt.-%, wt.-% with respect to the weight of the whole composition (including the solvent(s)).

Colouring the dental ceramic article is usually achieved by dipping the article into the solution. However, the solution can also be applied to the article by spraying, brushing, painting or by using a sponge or fabric.

The dental ceramic article is usually treated with the solution for about 1 to about 5 minutes, preferably from about 2 to about 3 minutes at room temperature (about 23° C.).

Preferably no pressure is used.

A penetration depth of the colouring solution into the dental ceramic article of about 5 mm is considered to be sufficient. The penetration depth can be determined as follows:

A plastic mesh (mesh size 500 μm) is located in a flat cup, which is filled with a colouring solution containing in addition a certain amount of a colourant (e.g. 100 ppm of Rhodamin B). A test bar of a presintered ceramic (LAVA™ Frame; 3M ESPE) having a size of Ø=about 24 mm, height=30 mm is placed on the plastic mesh and is soaked with the colouring solution for 2 min; dipping depth: 5 mm. The ceramic is taken out of the solution and is cut into slices. The cutting edges are finished and the penetration of the solution into the ceramic is analysed with a fluorescence microscope. If the added colourant can be detected over the whole range of the dipping depth and not only in a small border area (about 2 mm), the penetration behaviour of the solution is considered to meet the practitioner's needs.

Drying the coloured dental ceramic article is not absolute necessary, but can be preferred to reduce the time needed for firing and to avoid undesired inhomogenous colour effects. Drying can be effected by simply storing the dental ceramic article on a surface at ambient conditions for a couple of hours (about 1 to about 3 hours).

The ceramic article may also be produced by a process comprising the steps of mixing colouring components with ceramic components thereby obtaining a mixture and shaping the mixture to form a ceramic article.

The colouring and ceramic components are those, which are described in the present text.

Mixing of the components can be accomplished by means known to the person skilled in the art. Those means include e.g. mixing and optionally co-milling zirconia and colouring oxide particles (mixed oxide route); mixing zirconia particles and colouring oxide precursor substances, e.g. soluble nitrates and drying or respectively calcining the precursor e.g. in a fluidized bed reactor; co-precipitation of zirconia and colouring oxides, joint sol gel synthesis of zirconia and colouring oxides, joint gas phase synthesis of zirconia and colouring oxides and combinations thereof.

Shaping of the mixture can also be accomplished by means known to the person skilled in the art. Those means include e.g. uniaxial or isostatic compacting of preferably spray dried powders, slip casting, gel casting, extrusion and combinations thereof.

The process for producing the dental ceramic article may also comprise a sintering or firing step.

If conducted, the firing or sintering step should be accomplished under conditions which results in a dental ceramic article having an acceptable tooth like colour (e.g. a colour which fits into the Vita™ shade guide.

The firing conditions are dependant on the ceramic material used. A furnace which can be used is the commercially available LAVA™ Therm (3M ESPE). During the firing process the coloured dental ceramic framework is sintered to its final shape, thereby undergoing changes with regard to dimension, density, hardness, raw breaking resistance and/or grain size.

The firing usually takes place for a $ZrO_2$ based ceramic at a temperature above about 1100° C., above about 1300° C., preferably above about 1400° C., more preferably above about 1450° C. and lasts for at least about 0.5 h, preferably for at least about 1 h, more preferably for at least about 2 h. The firing temperature and dwell time (that is, the time period during which a particular temperature is kept) are typically correlated. A higher temperature typically requires only a short dwell time. Thus, the dwell time, may last from about 0 (e.g. if the firing temperature is about 1550° C.) to about 10 h (e.g. if the firing temperature is about 1100° C.) or from about 0.1 to about 8 h.

Generally, the sintering or firing conditions are adjusted such that the sintered dental ceramic article has a density of equal or greater than about 98% compared with the theoretically achievable density. In one embodiment this can be accomplished using a temperature above about 1300° C.

The ceramic article after a sintering step can usually be characterized by at least one or more of the following features:
Weibull strength (sigma 0): at least about 800 MPa, or at least about 900 MPa or at least about 1000 MPa,
L*a*b value:
L* in the range of about 65 to about 80 or in the range or about 67 to about 78,
a* in the range of about −1.5 to about 4 or in the range or about −1.1 to about 3.5,
b* in the range or about 5 to about 32 or in the range or about 7 to about 28,
measured as described in the text of the invention.

If desired, the L*a*b* values can be measure as described in the example section below.

Typically, the b value should be below about 32 or below about 28, whereas the values for L and a can be chosen more freely.

If desired, the Weibull strength (sigma 0) of the sintered dental ceramic article can be determined according to the "punch on three ball test" (biaxial flexural strength) described in DIN EN ISO 6872, edition March 1999, with the following modifications: diameter of steel ball: 6 mm; diameter of support circle: 14 mm; diameter of flat punch: 3.6 mm; diameter of sample disc: 19-20 mm, thickness of sample disc: 1.6 mm (+/−0.1 mm); no grinding and polishing of samples.

The invention also relates to a kit of parts comprising at least one ceramic article and at least one colouring solution, as described in the present text.

A kit of parts may facilitate the producing of the ceramic article as the individual parts which might be needed can be provided in a joint package.

The kit may provide more than one ceramic article (e.g. mill blank) and more than one colouring solution. E.g. the kit may comprise at least 2, 3, 4, 5, 6, 7, 8, 9, 10 colouring solutions, wherein the individual colouring solutions differ from each other by content and/or amount of colouring ions used. By providing a variety of different colouring solutions the dental practitioner can easily chose the colour he considers as appropriate for a certain dental restauration.

It can be beneficial if the kit also comprises a marker solution.

Such a marker solution can be used for temporarily enhancing the colour of a colouring solution. By temporarily enhancing the colour is meant that the marker solution contains colouring additives which disappear during a sintering or firing process, but remain until such a sintering or firing process is carried out.

Typical colouring additives for the marker solution include coloured organic substances, which are completely burned if heated to a temperature above about 450° C.

Useful colouring additives include anthocyan, betain, zuckercoleur, azo dyes and mixtures thereof. Those additives are also often used in food chemistry.

Besides colouring additives, the marker solution typically also comprises a solvent. Solvents which can be used include those which are described above with respect to the colouring solution. Besides solvent and colouring additives further adjuvants may by present (including viscosity modifiers and preservative agents).

The marker solution by be used for marking the colouring solution. If desired, the mixture of colouring solution and marker solution may be applied only to certain parts of the surface of the dental ceramic article (e.g. in the areas which may be close to the gum and thus may need particular attention and customized colouring).

Thus, a typical process for colouring a dental ceramic article comprises the steps of
providing a colouring solution and a marker solution,
mixing a part of the colouring solution with a part of the marker solution (e.g. a few drops), thereby obtaining a mixture,
applying the mixture to at least a part of the surface of the dental ceramic article.

According to a further embodiment, the invention relates to a kit of parts comprising part A and part B, part A comprising a colouring solution as described in the present text and part B comprising a marker solution as described in the present text.

A further aspect of the invention is directed to the use of a ceramic article or of a colouring solution in a colouring process. The colouring process comprises the step of treating the ceramic article with the colouring solution, wherein the ceramic article and the colouring solution are as described the present text.

A further aspect of the invention is directed to the use of a colouring solution for improving the brightness and/or decreasing the remission level of a ceramic article, the colouring solution and the ceramic article being as described the present text.

If desired, the brightness can be determined as described in the Example section below.

The dental article of the invention does typically not contain components or additives which jeopardize the intended purpose to be achieved with the present invention, i.e. providing an aesthetic dental restoration. Thus, components or additives added in an amount which finally results in a non-tooth-coloured article are usually not contained in the dental article. Typically, an article is characterized as not being tooth coloured if it cannot be allocated a colour from the Vita™ colour code system, known to the person skilled in the art. Additionally, components which reduce the mechanical strength of the dental restoration to a degree, where mechanical failure may occur, are also not included in the dental article.

The colouring solution of the invention does not necessarily comprise any organic colorants or colouring means that will only tint the surface but not the bulk, like pigments.

It is not mandatory, but if possible, the colouring solution should not or only contain a small amount of ingredients which can be detrimental to the firing equipment during the sintering process, like halogen (fluorine, chlorine, bromine or iodine). In this respect in certain embodiment of the present invention, the amount of halogen ions contained in the colouring solution should be kept low, e.g. below about 0.3 mol/l or below about 0.2 mol/l or below about 0.15 mol/l.

Moreover, in another embodiment of the invention, the colouring solution is essentially free of iron or iron ions. Thus, the content of iron or iron ions is usually below about 0.001 mol/l or below about 0.0001 or even below about 0.00001 mol/l solvent.

The following examples are given to illustrate, but not limit, the scope of this invention.

EXAMPLES

Unless otherwise indicated, all parts and percentages are on a weight basis, all water is deionized water, and all molecular weights are weight average molecular weight. Moreover, unless otherwise indicated all experiments were conducted at ambient conditions (23° C.; 1013 mbar).

The rare earth element containing compounds can be obtained e.g. from Aldrich, Merck or Fluka, Germany.

Crown Design Sample

Monolithic molar crowns were manufactured using a Lava™ CAD CAM system (3M ESPE, Germany) according to the instruction for use for monolithic zirconia restorations. The basic construction of the crowns is shown in FIG. 1. The thickness of the side walls (lingual, buccal, approximal) is about 0.8 mm. The thickness of the cusps (nearest distance from the cusp tip to the inner crown contour) is about 1.5 mm. The material thickness at the fissures is about 0.8 mm.

An appropriate full contour of a restoration according to the above mentioned geometric parameters can be designed in the Lava™ Design software 5.0. The same design was used for Examples 1a to 3a and Examples 1b to 3b, as described below. The design data were transferred into the CAM module and scaled according to the shrinkage value of particularly applied pre-sintered zirconia material. Then the crowns were milled out of blocks of the respective pre-sintered zirconia material on a Lava™ CNC 500 milling machine. The pre-sintered crowns were cut out of the blocks, cleaned by air blasting, shaded (details see below) and subsequently sintered in a high temperature furnace Lava™ Furnace 200 (details see below).

Example 1a: Lava™ Zirconia Crown Coloured with Lava™ Frame Shade to Yield an Approximate A2 Colour (Vita Classic Colour Schedule)—Al2O3 Content: 0.25 wt.-%

A crown according to the description above was milled out of a presintered Lava™ zirconia block (3M ESPE, Seefeld, Germany). The crown was coloured with a colouring solution composed of commercially available Lava™ Frame Shade 2 and Lava™ Frame Shade 3, 1/1, v/v) (3M ESPE, Seefeld, Germany) using a brush applicator.

The commercially available colouring solutions Lava™ Frame Shade 2 and Lava™ Frame Shade 3 include Er, Fe (but essentially no Mn or Pr).

The colouring was repeated three times at the cervical area, two times in the middle area of the lingual, buccal, approximal crown walls and was done once at the top of the crown, the incisal and occlusal areas. After 3 h drying at room temperature the crown was sintered according to instruction for use for Lava™ zirconia (1500° C. for 2 h).

Example 2a: Crystal HT Zirconia Blocks Coloured with Lava™ Frame Shades to Yield an Approximate A2 Colour (Vita™ Classic Colour Schedule)—Al2O3 Content: 0.05 wt.-%

A crown according to the description above was milled out of a presintered Crystal HT zirconia block (Dental Laboratory Milling Supplies, Scottsdale, Ariz., USA). The crown was coloured with a colouring solution composed of commercially available Lava™ Frame Shade 2 and Lava™ Frame Shade 3, 1/1, v/v) (3M ESPE, Seefeld, Germany) using a brush applicator.

The colouring was repeated three times at the cervical area, two times in the middle area of the lingual, buccal, approximal crown walls and was done once at the top of the crown, the incisal and occlusal areas. After 3 h drying at room temperature the crown was sintered according to instruction for use for Lava™ zirconia (1450° C. for 2 h).

Example 3a: Crystal HT Zirconia Blocks Coloured with the Inventive Shading Chemistry to Yield an Approximate A2 Colour (Vita™ Classic Colour Schedule)—Al2O3 Content: 0.05 wt.-%

A crown according to the description above was milled out of a presintered Crystal HT zirconia block (Dental Laboratory Milling Supplies, Scottsdale, Ariz., USA).

The crown was coloured with an experimental dyeing solution (0.26 mol/L erbium acetate, 0.01 mol/L praseodymium acetate, 0.005 mol/L manganese (II) chloride, 0.5427 mol/L triammonium citrate and 1.4989 wt.-% polyethylen glycol 35,000 in water) using a brush applicator.

The painting was repeated three times at the cervical area, two times in the middle area of the lingual, buccal, approximal crown walls and was done once at the top of the crown, the incisal and occlusal areas. After 3 h drying at room temperature the crown was sintered according to instruction for use for Lava™ zirconia (1450° C. for 2 h).

Example 1b

Same as Example 1a with exception of the colouring process: Instead of using a brush for colouring, the whole pre-sintered crown was immersed in the respective colouring liquid for about 2 min.

Example 2b

Same as Example 2a with exception of the colouring process: Instead of using a brush for colouring, the whole pre-sintered crown was immersed in the respective colouring liquid for about 2 min.

Example 3b

Same as Example 3a with exception of the colouring process: Instead of using a brush for colouring, the whole pre-sintered crown was immersed in the respective colouring liquid for about 2 min.

Visualization of the Aesthetic Improvements in a Demonstrator

Figure 2A:
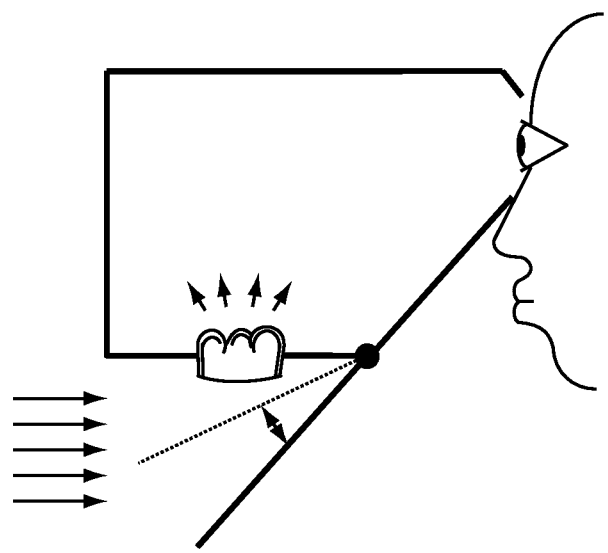
FIG. 2a shows a construction of a demonstrator suitable to visualize the differences of light transmission between coloured crowns.
Figure 2B:
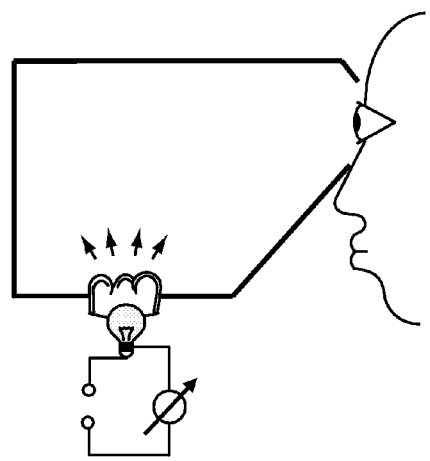
FIG. 2b shows another construction of a demonstrator suitable to visualize the differences of light transmission between coloured crowns.

FIG. 2a and FIG. 2b show embodiments of demonstrators which are suitable to visualize the aesthetic improvements which can be achieved with the invention.

Basically, the demonstrators are boxes with an optical neutral inner surface (grey or black). The box has an opening just big enough allowing the viewer to look into the interior. On the opposite side of the viewer openings are located for the crown samples to be inspected (e.g. 3 crown openings for 3 crowns). These openings have essentially the same lateral dimension as crowns in order to avoid that light between the crowns and the box gets into the interior. Preferably the edges of crown openings are made of an elastic material like rubber so that the crowns simultaneously are mechanically fixed. With this setup the viewer is shielded from the ambient light and can concentrate on differences in the light transmission behaviour of the crown samples. The illumination of the crown samples simply can be achieved by daylight (FIG. 2a). Optionally, the intensity of the lighting can be adjusted by a simple flap, preferable of a white carton. Another way is to place electrical lamps behind the crowns e.g. D64 lamps or daylight LEDs (FIG. 2b).

Results

When comparing the samples of Examples 1a, 2a and 3a in a demonstrator described above it was found that the sample of Example 3a looked brighter than the sample of Example 2a and that the sample of Example 2a looks brighter than the sample of Example 1a. Especially, in the area of the cusps a difference of illumination could be observed, an effect which could not have been expected.

The effect was similar when the samples of Examples 1b, 2b and 3b were compared with each other.

General Preparation of Coloured Platelet Samples

Cylinders of pre-sintered materials (diameter 17 mm, height according to height of the used block) are milled on a Lava™ System (Lava™ CNC500, 3M ESPE, Germany). Subsequently platelets of about 2.2 to 2.4 mm thickness are dry sawed from the cylinders on a Cutman 100 saw (Renfert Corp., Germany). The pre-sintered platelets are cleaned by air blasting and then dipped in the respective colouring solution for about 2 min. After removing the platelets out of the immersion bath residual colouring solution on the platelets is soaked with a paper tissue. The platelets are dried for about 3 h at room temperature and then are sintered to full density in a high temperature furnace (Lava™ Furnace 200, 3M ESPE) on a alumina plate powdered with alumina grains WSK24 (Treibacher, Austria) according to the material specific sinter protocol. The final thickness of the platelets then is roughly adjusted to 1.5 mm by grinding on Smart N6 Comfort 5 grinding machine (Elbschliff Corp., Germany) using a D64 and D10 diamond grinding disks (Effgen Corp., Germany). Fine adjustment to 1.50 (+/−0.03) mm thickness and surface finishing is done by polishing on a Spectrum 1000 polishing machine (Leco Corp., USA) using a 9 µm diamond suspension (Ziesmer Corp., Germany) on a polishing cloth (Bühler, Germany).

Example 4: Platelets of Lava™ Zirconia Coloured with Lava™ Frame Shade to Get a Colour Close to A2 (Vita™ Classic Colour Schedule)—Al2O3 Content: 0.25 wt.-%

Platelets were prepared from a Lava™ zirconia block (3M ESPE, Seefeld, Germany), coloured with a composition of Lava™ Frame Shade 2 and Lava™ Frame Shade 3, 1/1, v/v (3M ESPE, Seefeld, Germany) and sintered according to Instructions for Use up to 1500° C. for 2 h.

Example 5: Platelets of Crystal HT Zirconia Coloured with Lava™ Frame Shade to Get a Colour Close to A2 (Vita™ Classic Colour Schedule)—Al2O3 Content: 0.05 wt.-%

Platelets were prepared from presintered Crystal HT zirconia block (Dental Laboratory Milling Supplies, Scottsdale, Ariz., USA) and coloured with a composition of Lava™ Frame Shade 2 and Lava™ Frame Shade 3, 1/1, v/v (3M ESPE, Seefeld, Germany) and sintered according to instructions for use (Crystal HT zirconia) up to 1450° C. for 2 h.

Example 6: Platelets of Crystal HT Zirconia Coloured with the Inventive Shading Chemistry Chemistry in Order to Get a Colour Close to A2 (Vita Classic Colour Schedule)—Al2O3 Content: 0.05 wt.-%

Platelets were prepared from presintered Crystal HT zirconia block (Dental Laboratory Milling Supplies, Scottsdale, Ariz., USA) and dyed with an experimental dyeing solution (0.26 mol/L erbium acetate, 0.01 mol/L praseodymium acetate, 0.005 mol/L manganese (II) chloride, 0.5427 mol/L triammonium citrate and 1.4989 wt.-% polyethylen glycol 35,000 in water) and sintered according to Instructions for Use (Crystal HT zirconia) up to 1450° C. for 2 h.

Remission Spectra of Examples 4, 5 and 6

The spectra were recorded on an X-rite Colour i7 spectrophotometer device (X-rite Corp., USA) equipped with a D65 light source using the following settings. Setup measurement geometry: Remission against black background (R/T Mode: OL/OD), specula excluded (SPE), area views 10 mm (MAV), UV irradiation on, lens=S).

Figure 3:
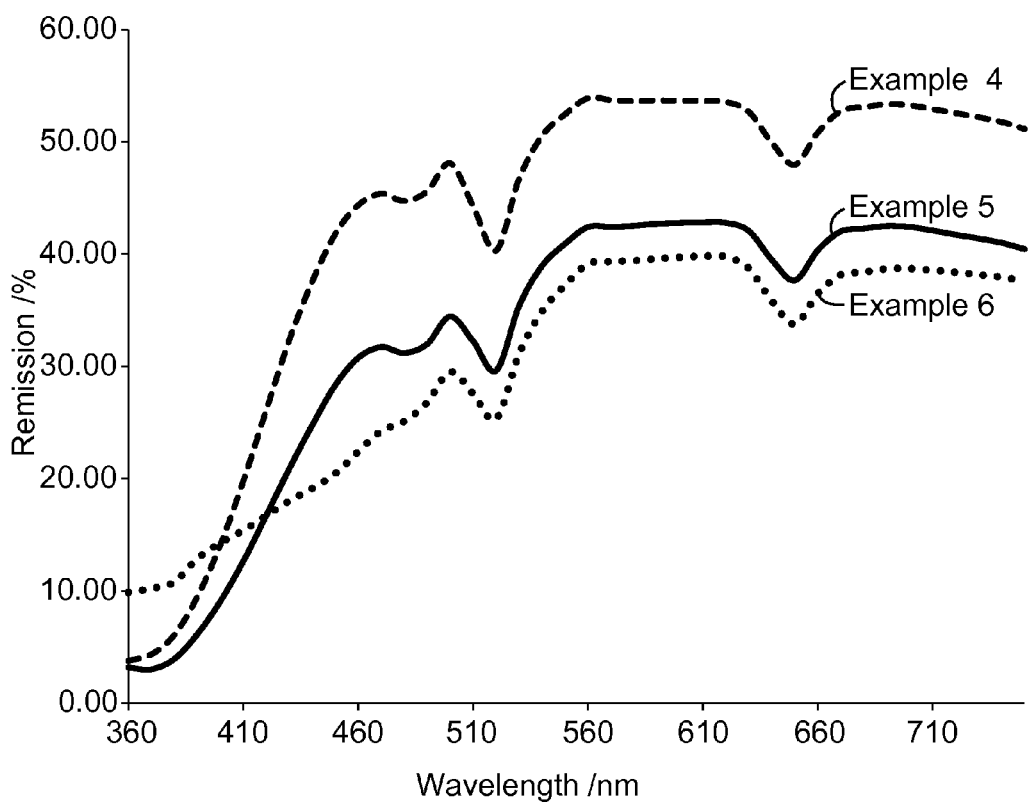
FIG. 3 shows a remission spectrum of dental ceramic articles coloured with different colouring solutions.

In order to obtain a simple measure for the overall intensity of the backscattered light the spectra were numerically integrated between 400 and 700 nm yielding a numerical backscatter value (NBV) in arbitrary units. The spectra are shown in FIG. 3.

Lava™ zirconia coloured with Lava™ Frame Shade showed the highest remission level (Example 4) with a NBV of about 8700. For Crystal HT coloured with Lava™ Frame Shade (Example 5) the NBV was lower at about 6400 whereas the lowest level of backscattering was observed with Crystal HT coloured with the experimental colouring liquid (Example 6) yielding a NBV of about 5600.

The lower the remission level determined, the better the light transmission and/or brightness typically is.

The invention claimed is:

1. A pre-sintered dental ceramic article comprising ceramic components, the ceramic components comprising ZrO2 and Al2O3 and colouring components comprising ions or oxides of Mn, Er, or mixtures thereof, wherein the pre-sintered dental ceramic article has:
Al2O3: from 0.01 to about 0.12 wt.-%;
Er2O3: from about 0.010 wt.-% to about 1.5 wt.-%;
Pr6O11: from about 0 wt.-% to about 0.1 wt.-%;
MnO2: from about 0.001 wt.-% to about 0.01 wt.-%; and
Fe2O3: 0 wt.-% to about 0.1 wt.-%, wherein wt.-% is with respect to the weight of the ceramic article.

2. The dental ceramic article of claim 1, comprising a stabilizer selected from oxides of Y, Mg, Ca, Ce, La and mixtures thereof.

3. The dental ceramic article of claim 1, wherein the ceramic article has the shape of a dental support structure, a dental crown, a dental bridge, a dental facing, an inlay, an inlay, a mill blank, an implant or an abutment.

4. The dental ceramic article of claim 1, wherein the dental ceramic is contained in a frame or a holding device.

5. The dental ceramic article of claim 1 being characterized by at least one of the following features:
density: from about 2.4 to about 3.7 g/cm$^3$; or
porosity: from about 40 to about 60 vol.-%.

6. The dental ceramic article according to claim 1, wherein the dental ceramic article comprises pores having diameters from about 50 nm to about 150 nm.

7. The dental ceramic article according to claim 1, wherein Al2O3 is present in an amount below about 0.1 wt.-% with respect to the weight of the ceramic components.

8. A sintered dental ceramic article comprising ceramic components, the ceramic components comprising ZrO2 and Al2O3 and colouring components comprising ions or oxides of Mn, Er, or mixtures thereof, wherein Al2O3 is present in an amount from about 0.01 to about 0.15 wt. % with respect to the weight of the ceramic components and wherein the sintered dental ceramic article has:
 ZrO2+HfO2: from about 80 wt.-% to about 98 wt.-%;
 Al2O3: from 0.01 to about 0.12 wt.-%;
 Er2O3: from about 0.010 wt.-% to about 1.5 wt.-%;
 Pr6O11: from about 0 wt.-% to about 0.1 wt.-%;
 MnO2: from about 0.001 wt.-% to about 0.01 wt.-%; and
 Fe2O3: 0 wt.-% to about 0.1 wt.-%,
 wherein wt.-% is with respect to the weight of the sintered dental ceramic article and the sintered dental ceramic article has at least one of the following features:
 breaking resistance: at least about 400 MPa;
 density: from about 5.9 to about 6.1 g/cm$^3$ or
 fluorescence emission in the region of the visible light.

9. A process for producing a dental ceramic article, the process comprising the step of treating a ceramic article with a colouring solution, wherein the ceramic article comprises ZrO2 and Al2O3, and
 the colouring solution comprises at least one colouring component comprising ions selected from Er, Mn and mixtures thereof and sintering the treated ceramic article such that the sintered dental ceramic article has:
 ZrO2+HfO2: from about 80 wt.-% to about 98 wt.-%;
 Al2O3: from 0.01 to about 0.12 wt.-%;
 Er2O3: from about 0.010 wt.-% to about 1.5 wt.-%;
 Pr6O11: from about 0 wt.-% to about 0.1 wt.-%;
 MnO2: from about 0.001 wt.-% to about 0.01 wt.-%; and
 Fe2O3: 0 wt.-% to about 0.1 wt.-%,
 wherein wt.-% is with respect to the weight of the sintered dental ceramic article.

10. The process of claim 9 wherein the step of sintering the ceramic article after treatment with the colouring solution is at a temperature within a range from about 1300° C. to about 1550° C., optionally with a dwell time from about 0 to about 10 h.

11. A process for producing a dental ceramic article, the process comprising the steps of mixing at least one colouring component with ceramic components thereby obtaining a mixture, the at least one colouring component comprising ions or oxides selected from Er, Mn and mixtures thereof, the ceramic components comprising ZrO2 and Al2O3,
 shaping the mixture to form a ceramic article and optionally sintering the ceramic article
 wherein the ceramic article has:
 ZrO2+HfO2: from about 80 wt.-% to about 98 wt.-%;
 Er2O3: from about 0.010 wt.-% to about 1.5 wt.-%;
 Pr6O11: from about 0 wt.-% to about 0.1 wt.-%;
 MnO2: from about 0.001 wt.-% to about 0.01 wt.-%; and
 Fe2O3: 0 wt.-% to about 0.1 wt.-%,
 wherein wt.-% is with respect to the weight of the dental ceramic article.

* * * * *

UNITED STATES PATENT AND TRADEMARK OFFICE
CERTIFICATE OF CORRECTION

PATENT NO.         : 9,758,435 B2
APPLICATION NO.    : 14/003409
DATED              : September 12, 2017
INVENTOR(S)        : Gallus Schechner et al.

It is certified that error appears in the above-identified patent and that said Letters Patent is hereby corrected as shown below:

On the Title Page

Column 2
Line 8, (Abstract), delete "coloring" and insert -- colouring --, therefor.

Column 1
Page 3, (Other Publications), Line 5, delete "(PMDS)" and insert -- (PDMS) --, therefor.

Column 2
Page 3, (Other Publications), Line 26, delete "Photopolymerizabel" and insert
-- Photopolymerizable --, therefor.

Column 2
Page 3, (Other Publications), Line 54, delete "vol. I:;" and insert -- vol. I: --, therefor.

Column 2
Page 4, (Other Publications), Line 2, delete "Denturs:" and insert -- Dentures: --, therefor.

Column 2
Page 4, (Other Publications), Line 7, delete "Chemi" and insert -- Chemie --, therefor.

In the Specification

Column 1
Line 55, delete "wt %" and insert -- wt.-% --, therefor.

Column 1
Line 64, delete "Hospitoal)" and insert -- Hospital) --, therefor.

Signed and Sealed this
Eighth Day of May, 2018

Andrei Iancu
*Director of the United States Patent and Trademark Office*

Column 3
Line 8, delete "sample" and insert -- sample. --, therefor.

Column 3
Line 62, delete "former" and insert -- former. --, therefor.

Column 6
Line 4, delete "willfully" and insert -- wilfully --, therefor.

Column 8
Line 67, delete "exitation" and insert -- excitation --, therefor.

Column 9
Line 46, delete "solution" and insert -- solution. --, therefor.

Column 9
Line 57, delete "mol/L" and insert -- mol/L. --, therefor.

Column 11
Line 7, delete "polyethylenglycols" and insert -- polyethyleneglycols --, therefor.

Column 12
Line 4, delete "polyethylenglycols" and insert -- polyethyleneglycols --, therefor.

Column 12
Line 18, delete "inhomogenous" and insert -- inhomogeneous --, therefor.

Column 13
Line 47, delete "restauration." and insert -- restoration. --, therefor.

Column 13
Line 59, delete "betain," and insert -- betaine, --, therefor.

Column 13
Line 60, delete "zuckercoleur," and insert -- zuckercouleur, --, therefor.

Column 14
Line 59, after "0.0001" insert -- mol/l --.

Column 16
Lines 16-17, (approx.), delete "polyethylen" and insert -- polyethylene --, therefor.

Column 18
Line 2, after "Shading" delete "Chemistry".

CERTIFICATE OF CORRECTION (continued)
U.S. Pat. No. 9,758,435 B2

Column 18
Lines 12-13, delete "polyethylen" and insert -- polyethylene --, therefor.

Column 18
Line 23, delete "specula" and insert -- specular --, therefor.

In the Claims

Column 19
Lines 7-9, in Claim 8, after "thereof," delete "wherein Al2O3 is present in an amount from about 0.01 to about 0.15 wt. % with respect to the weight of the ceramic components and".